(12) United States Patent  
Wolkin et al.

(10) Patent No.: US 9,212,982 B2  
(45) Date of Patent: Dec. 15, 2015

(54) MATTRESS TESTING APPARATUS AND METHOD

(71) Applicant: Colgate Atlanta Mattress Corporation, Atlanta, GA (US)

(72) Inventors: Richard H Wolkin, Atlanta, GA (US); James Hewatt, Lilburn, GA (US)

(73) Assignee: COLGATE ATLANTA MATRESS CORPORATION, Atlanta, GA (US)

( * ) Notice: Subject to any disclaimer, the term of this patent is extended or adjusted under 35 U.S.C. 154(b) by 41 days.

(21) Appl. No.: 14/277,148

(22) Filed: May 14, 2014

(65) Prior Publication Data

US 2014/0238104 A1   Aug. 28, 2014

Related U.S. Application Data

(63) Continuation-in-part of application No. 14/048,997, filed on Oct. 8, 2013.

(60) Provisional application No. 61/711,909, filed on Oct. 10, 2012.

(51) Int. Cl.
| | |
|---|---|
| *G01N 3/30* | (2006.01) |
| *G01N 3/00* | (2006.01) |
| *G01N 3/32* | (2006.01) |
| *G01N 3/40* | (2006.01) |
| *G01M 99/00* | (2011.01) |

(52) U.S. Cl.
CPC ............... *G01N 3/32* (2013.01); *G01M 99/001* (2013.01); *G01N 3/40* (2013.01)

(58) Field of Classification Search
None
See application file for complete search history.

(56) References Cited

U.S. PATENT DOCUMENTS

| | | | | |
|---|---|---|---|---|
| 3,195,347 | A * | 7/1965 | Janapol | 73/806 |
| 3,413,849 | A * | 12/1968 | Janapol | 73/161 |
| 4,004,457 | A | 1/1977 | Eide et al. | |
| 4,140,008 | A | 2/1979 | Golembeck | |
| 6,786,083 | B1 * | 9/2004 | Bain et al. | 73/78 |
| D530,639 | S | 10/2006 | Conigliaro | |

OTHER PUBLICATIONS

ASTM, D:F-1566-99 (Reapproved 2004), STM for Evaluation of Innersprings and Boxsprings, 8 pages.
Standards Australia/Standards New Zealand, DR AS/NZS 8811.1, Methods of testing infant products Part 1: Sleep surfaces—Test for firmness (Draft for Public Comment), 9 pages, Aug. 14, 2012.

* cited by examiner

*Primary Examiner* — Lisa Caputo
*Assistant Examiner* — Brandi N Hopkins
(74) *Attorney, Agent, or Firm* — Thomas B. McGurk

(57) ABSTRACT

An apparatus and method of testing are provided to test the durability and resilience of crib mattresses and other child development surfaces. The testing apparatus is configured to provide a movable fixture for imparting repeated force to a mattress. The fixture can include a pair of feet formed thereon to mimic the pressure profile provided by a toddler standing or jumping on a crib mattress. The method provides for the cycling of the apparatus over a predetermined time period and the determination of the deflection of the surface after the time period.

13 Claims, 14 Drawing Sheets

MATTRESS TESTING APPARATUS AND METHOD

RELATED APPLICATIONS

This application is a continuation-in-part of U.S. Non-provisional application Ser. No. 14/048,997, filed Oct. 8, 2013, which claims the benefit of priority to U.S. Provisional Application No. 61/711,909, filed Oct. 10, 2012. Both the U.S. Non-provisional application and this Provisional application identified above are hereby incorporated by reference in their entirety herein to provide continuity of disclosure.

TECHNICAL FIELD

The following disclosure is directed to mattress testing apparatus and methods. In particular, the present disclosure is directed to apparatus and methods for testing crib mattresses and flexible child development surfaces and platforms, as well as other furniture.

BACKGROUND

At present, there are no satisfactory test procedures or testing machinery available that can be used to evaluate the ability of a crib mattress to withstand the normal use by a toddler or infant. A crib mattress is not just a sleeping surface for an infant. A crib mattress also is a developmental center for a growing baby and toddler. While an infant usually just sleeps or lies on a crib mattress, a toddler can engage in variety of activities besides sleeping while on a crib mattress. Toddlers typically crawl, walk, and jump on the surface of the mattress while in their cribs. Both the frequency and the force exerted by a toddler jumping upon on a crib mattress surface can be significant. Toddlers can weigh 13 kg or more, and are capable of repeatedly jumping and then dropping approximately 20 cm or more onto the surface of the crib mattress while in their cribs. Depending upon the give in a mattress, a typical toddler jump could apply approximately 1080 N to a mattress surface. There was a need to develop apparatus and methods for testing the durability of crib mattresses when subjected to such repeated forces.

Furthermore, the safety of a crib mattress requires assessment not only when new, but after normal use. Gaps between a crib mattress and the side of a crib may increase as the mattress becomes worn and deforms from its original configuration by the weight of the toddler impacting the surface.

Consequently, there is a need for testing apparatus and test methods by which the durability, compression resilience, and/or safety of a crib mattress surface and components can be evaluated.

SUMMARY

The present disclosure encompasses an apparatus for testing a crib mattress comprising a frame, a mattress support member disposed on the frame, and a fixture movably mounted to the frame. The fixture is disposed above the mattress support member and is movable from a first position proximal to the mattress support member to a second position distal to the mattress support member. In another aspect, the fixture comprises a pair of legs formed thereon, with each leg of the pair of legs having a foot formed thereon. The apparatus also can comprise a cable connected to the fixture and mounted on the frame, wherein the fixture is suspended by the cable from the fixture, as well as a shuttle connected to the cable, and, alternatively a raceway mounted on the frame and wherein the shuttle is movably aligned within the raceway. The apparatus also can include a chain loop mounted on the frame, wherein the chain loop comprises a catch attached thereto, wherein the shuttle is movably engagable with the catch. In another aspect, the apparatus can include a detachable load member mounted on the fixture, and, alternatively, a motor operably connected to the fixture. In another aspect, the apparatus can include a mattress support member with a movable sidewall. Furthermore, the fixture can comprise a guide rail. In another aspect, the apparatus can comprise a guide bracket mounted to the frame and wherein the guide rail is movably aligned within an aperture in the guide bracket. Additionally, a flexible layer can be disposed on the bottom of at least one of the feet.

The present disclosure also can encompass a mattress testing apparatus comprising a frame, a fixture suspended from the frame, wherein the fixture comprises a pair of feet, a motor mounted on the frame and operably connected to the fixture, wherein the fixture is reciprocally movable by the motor vertically between a first position adjacent a sample target area and a second elevated position, and wherein the fixture is movable from the second elevated position to the first position by gravity. The testing apparatus also can comprise a mattress support member disposed below the fixture. Furthermore, the mattress support member can comprise a movable sidewall. Additionally, the mattress testing apparatus can comprise a flexible layer disposed on the bottom of at least one of the feet. The mattress testing apparatus also can comprise a cable connected to the fixture and mounted to the frame. Furthermore, the fixture of the mattress testing apparatus can comprise a guide rail.

The present disclosure also encompasses a crib mattress testing apparatus comprising a frame comprising an arm, a fixture mounted on the arm of the frame, the fixture comprising a pair of legs, wherein each of the pair of legs comprises a foot attached thereto, a cable connected to the fixture and mounted to the frame, wherein the fixture is suspended from the frame by the cable, and a crib mattress support member mounted on the frame, wherein the crib mattress support member comprises a movable sidewall. The apparatus also comprises a motor operably connected to the cable, wherein the motor is operably engaged to the fixture to move reciprocally the fixture vertically between a first position proximal to the crib mattress support member to a second position distal to the crib mattress support member, and wherein the fixture is movable by gravity from the second position to the first position.

The present disclosure also encompasses a method of testing a crib mattress comprising the steps of aligning a mattress under a fixture of a test apparatus, placing a platen on a top surface of the mattress, wherein the platen comprises a first opening and a second opening formed therein, and wherein each of the first and the second openings are aligned over one of a first position and a second position on the top surface of the mattress, placing a measurement form in the first opening, wherein the measurement form contacts the top surface of the mattress, and measuring a first distance from the top surface of the mattress to a first pre-determined point on the platen. The method also comprises the steps of placing the measurement form in the second opening, wherein the measurement form contacts the top surface of the mattress, measuring a first distance from the top surface of the mattress to a second pre-determined point on the platen, contacting the first and the second positions on the top surface of the mattress with a fixture having a pair of feet formed thereon, and removing the fixture from the top surface of the mattress. The method further comprises the steps of placing the platen on the top surface of the mattress, and wherein each of the first and the second openings are aligned over one of the first position and the second position on the top surface of the mattress, placing the measurement form in the first opening, wherein the measurement form contacts the top surface of the mattress, measuring a second distance from the top surface of the mattress to the first pre-determined point on the platen, placing the measurement form in the second opening, wherein the measurement form contacts the top surface of the mattress, and measuring a second distance from the top surface of the mattress to the second pre-determined point on the platen. The method still further comprises determining a differential between the first distance and the second distance from the top surface of the mattress to the first pre-determined point on the platen, and determining a differential between the first distance and the second distance from the top surface of the mattress to the second pre-determined point on the platen. In another aspect, the method can further comprise dropping the fixture onto the top surface of the mattress from a predetermined height during the step of contacting the first and the second positions on the top surface of the mattress with a fixture having a pair of feet formed thereon. Additionally, the method can further comprise marking a position of the platen on the top surface of the mattress. In another aspect, the first pre-determined point on the platen can be a top edge of the first opening, and, alternatively, the second pre-determined point on the platen can be a top edge of the second opening. Furthermore, each of the first and the second openings can be disposed within one of a first and a second shoe print formed on the platen. In yet another aspect, the first position and the second position can be aligned below one of a first foot and a second foot of the pair of feet of the fixture. Additionally, the step of measuring a first distance from the top surface of the mattress to a first pre-determined point on the platen further can comprise reading the first distance from measurement indicia formed on the measurement form.

The present disclosure additionally encompasses a method of testing a crib mattress comprising the steps of aligning a mattress under a fixture of a test apparatus, placing a platen on a top surface of the mattress, wherein the platen comprises an opening formed therein, and the opening is aligned over a position on the top surface of the mattress, placing a measurement form in the opening, wherein the measurement form contacts the top surface of the mattress, measuring a first distance from the top surface of the mattress to a pre-determined point on the platen, contacting the position on the top surface of the mattress with a fixture, removing the fixture from the top surface of the mattress, placing the platen on the top surface of the mattress, and wherein the opening is aligned over the position on the top surface of the mattress, placing the measurement form in the opening, wherein the measurement form contacts the top surface of the mattress, measuring a second distance from the top surface of the mattress to the pre-determined point on the platen, and, determining a differential between the first distance and the second distance from the top surface of the mattress to the pre-determined point on the platen. Furthermore, the method can comprise dropping the fixture onto the top surface of the mattress from a predetermined height during the step of contacting the first and the second positions on the top surface of the mattress with a fixture having a pair of feet. Additionally, the method of can further comprise marking a position of the platen on the top surface of the mattress. In another aspect, the pre-determined point on the platen can be a top edge of the opening. Also, the method can further comprise reading the first distance from measurement indicia formed on the measurement form during the step of measuring a first distance from the top surface of the mattress to a pre-determined point on the platen.

Other objects, advantages and features of the present disclosure are encompassed by the following description and drawings, which are briefly described as follows.

DETAILED DESCRIPTION

Figure 1:
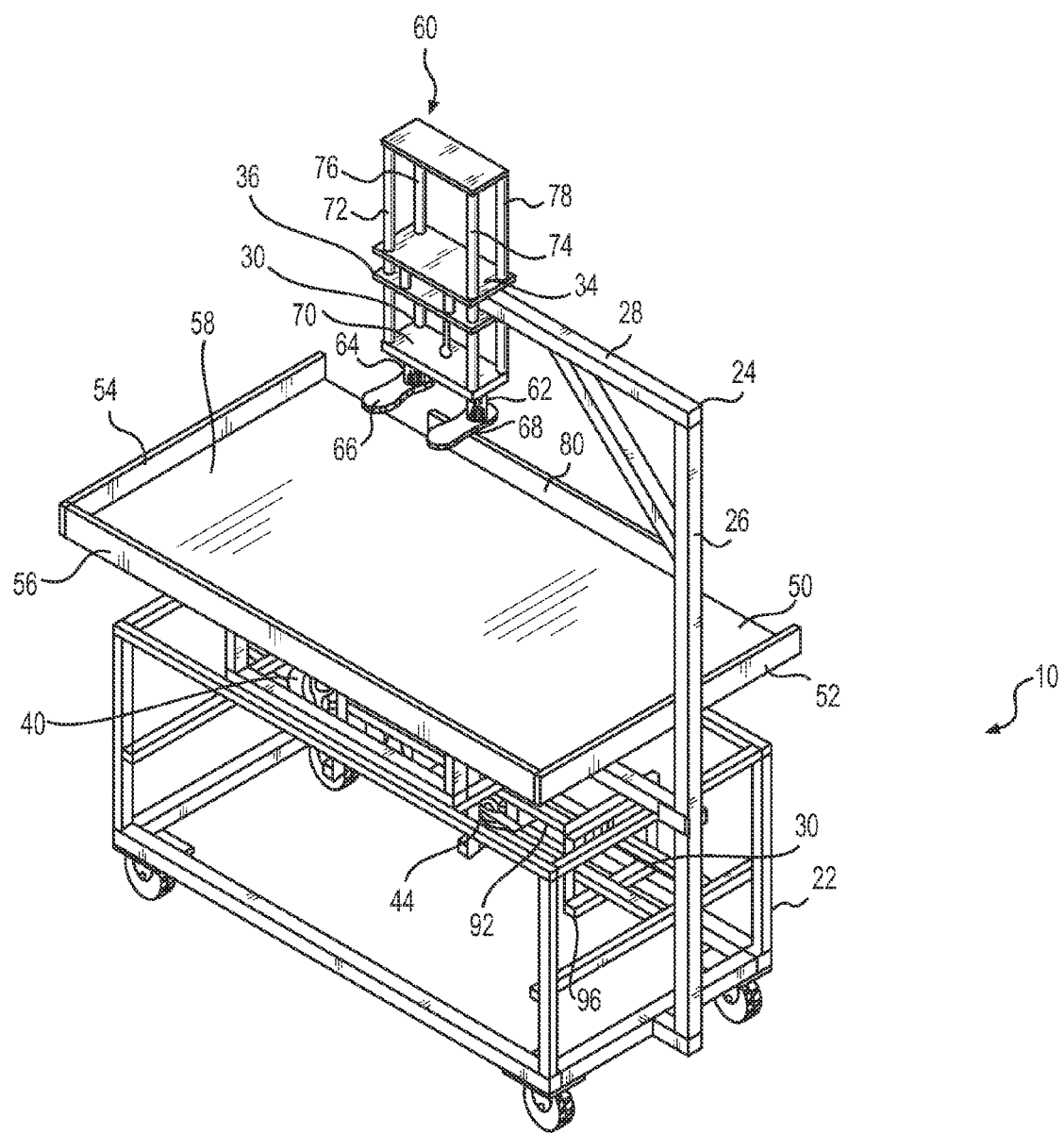
FIG. 1 is a perspective view of a testing apparatus encompassing aspects of the present disclosure.

An apparatus for testing one or more characteristics of a crib mattress or other flexible child development surface or platform and/or components thereof is disclosed herein. The apparatus generally can include a sample support and a force-generating member. The force-generating member can move in at least one plane relative to the sample support so as to allow for the application of force to a sample disposed on the support. The sample can be a crib mattress or other flexible child development platform or component thereof. The present disclosure also encompasses apparatus and methods for testing other types of structures to which repeated forces can be applied in the course of use.

In one aspect, the force-generating member includes a pair of contact forms that contact the surface of the sample when force is applied thereto. The contact forms, in one embodiment, can be aligned and configured to replicate the positioning and size of a typical toddler legs and feet. The force-generating member can include a movable fixture having a pre-determined mass and/or configuration. The force-generating member can employ gravity to generate the force applied to the sample. The apparatus can include a movable fixture having formed thereon or attached thereto a pair of sample-contacting surfaces. The sample-contacting surfaces can be spaced apart a distance that would be similar to the spacing of the feet of a typically sized toddler when standing. The sample-contacting surfaces may be shaped to have a general foot-like outline. Each sample-contacting surface can be connected to the movable fixture by a leg generally aligned to the rear of the surface, so that force applied to each surface is distributed along the extent of the surface in a manner similar to the distribution of a child's weight on the bottoms of his or her feet when standing.

A method for testing one or more characteristics of a crib mattress or other flexible child development surface or platform and/or component thereof is disclosed herein. The method generally can include selecting a sample of a crib mattress or other flexible child development surface or platform or component thereof. The method also includes aligning the sample in position for a force to be applied thereto by a force-generating member. The method further includes applying a predetermined force to two portions of the sample. The method also includes removing the force from the two portions of the sample. The method also can include repeating a cycle of application to and removal of a force from the portions of the sample. The method can include executing multiple force cycles. The executing of multiple force cycles can include executing a predetermined number of force cycles. The executing of the multiple force cycles also can include applying the force to the two portions of the sample for a predetermined period of time. The method may further include removing the force from two portions of the sample for a predetermined period of time prior to a subsequent application of a force to the portion of the sample.

Among the various aspects that can be evaluated are the durability and compression resistance of a crib mattress and/or its constituent components. Various aspects of the safety of a combination of a crib and mattress also can be evaluated by the apparatus and methods encompassed by the present disclosure.

Figure 12:
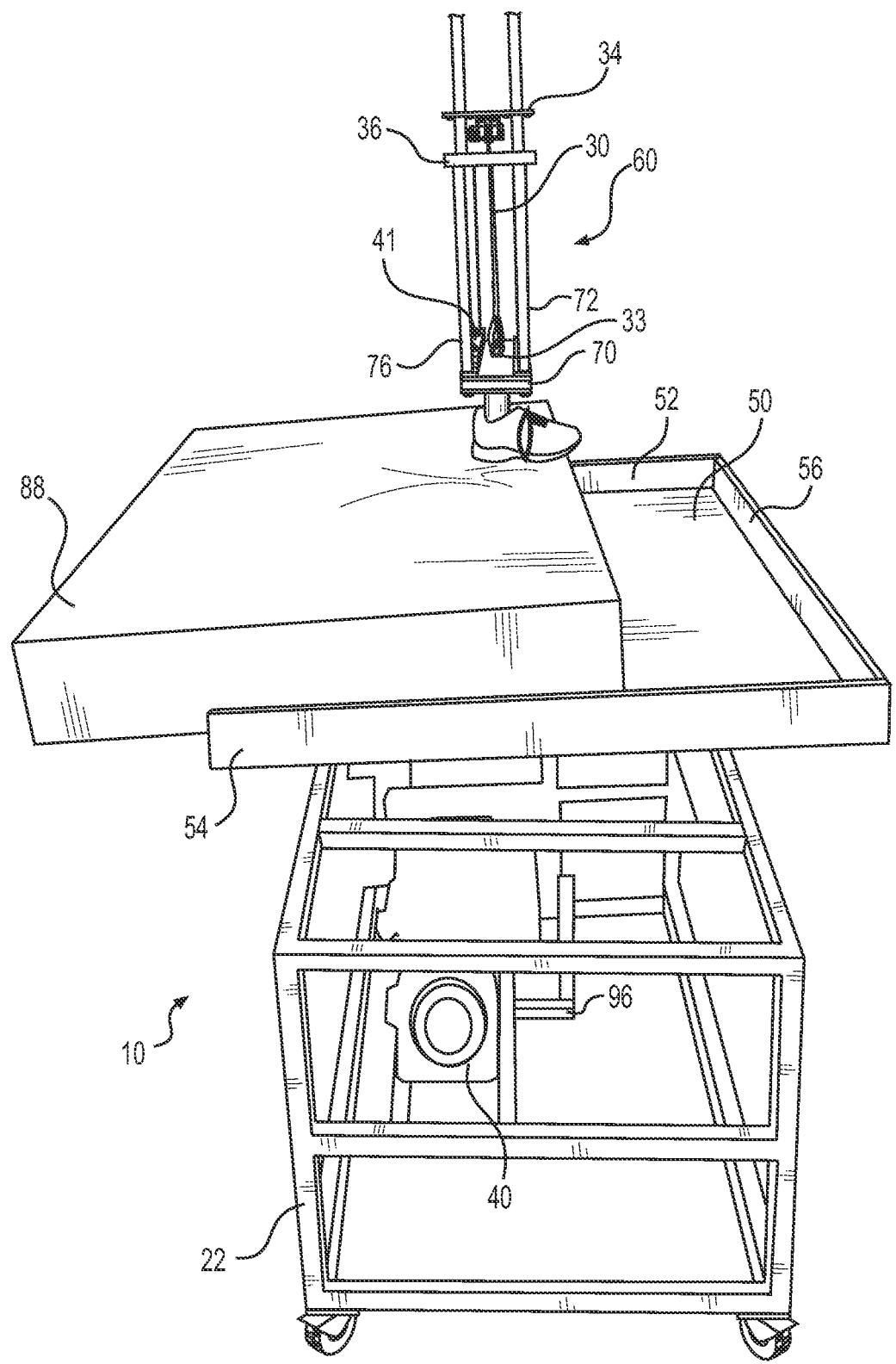
FIG. 12 is a perspective view of the testing apparatus shown in FIG. 9 with a crib mattress placed thereon.

FIG. 1 shows an apparatus 10 that encompasses aspects of the present disclosure. The apparatus 10 includes a frame 22 mounted on castors and supporting a motor 40, a cable assembly operably connected to the motor 40 and a fixture 60 mounted on a support arm 24 attached to the frame 22. The fixture 60 is attached to a cable 30 that is operably connected to the cable assembly and motor 40. The apparatus 10 also includes a mattress support member 50 disposed below the fixture 60. As shown in FIGS. 1, 2, 9, and 12, the mattress support member 50 can include a planar platform with vertical sidewalls 52, 54, 56. The mattress support member 50 also can include a movable sidewall 80. The movable sidewall 80 can be moved from a vertical position, as shown in FIG. 1 to a horizontal position to accommodate a sample mattress in a position as shown in FIG. 12.

Figure 2:
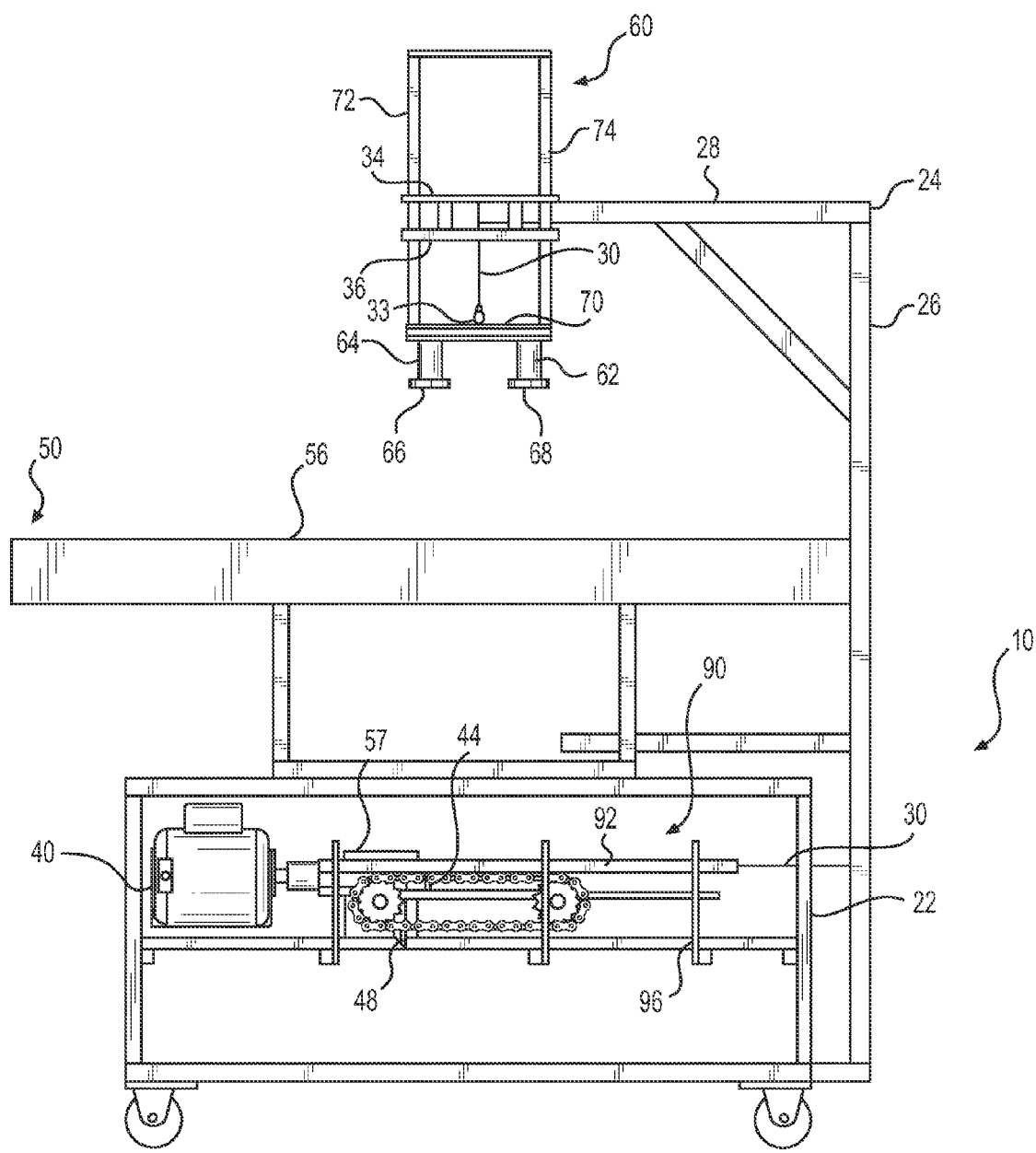
FIG. 2 is a side elevation view of a testing apparatus encompassing aspects of the present disclosure.
Figure 3:
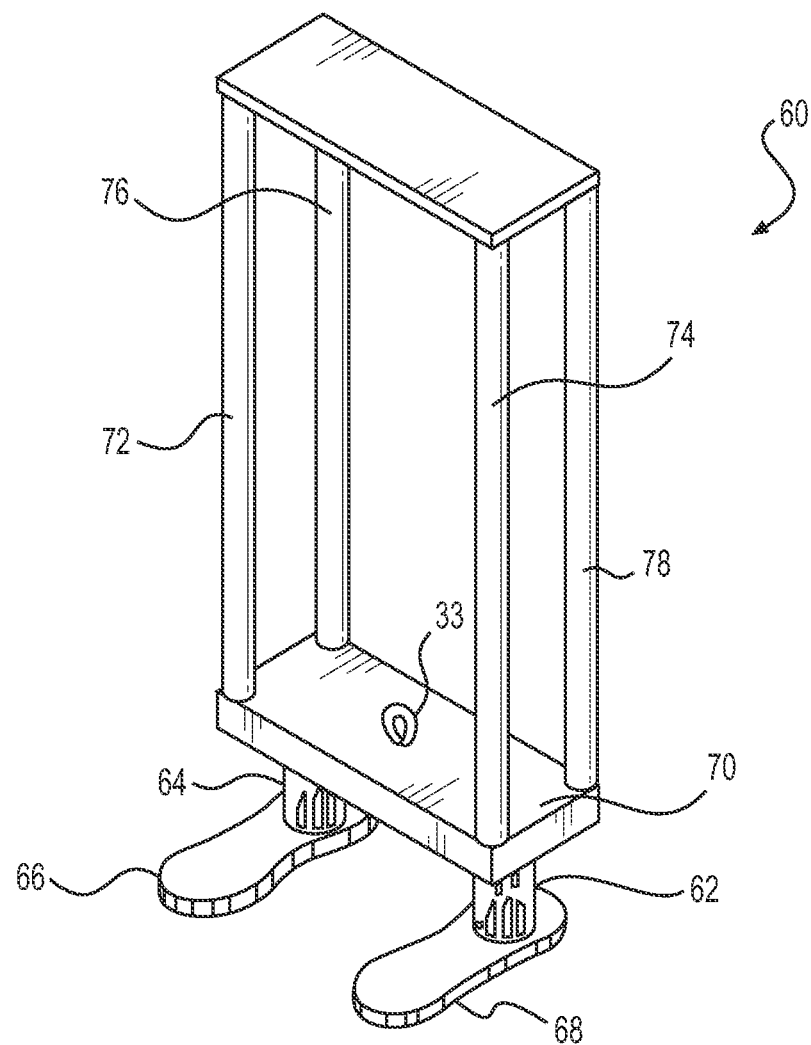
FIG. 3 is a perspective view of a fixture for a testing apparatus encompassing aspects of the present disclosure.

As shown in FIGS. 1, 2 and 3, the fixture 60 includes a fixture base 70 to which is attached a plurality of guide rails and upon which detachable load members can be attached. In the embodiment shown, the plurality of guide rails include a first guide rail 72, a second guide rail 74, a third guide rail 76, and a fourth guide rail 78. The four guide rails are aligned in a generally rectangular arrangement and extend perpendicular from the upper surface of the fixture base 70. The present disclosure encompasses other numbers and configurations of guides, and in at least one embodiment can include no guides. The guide rails 72, 74, 76, and 78 are movably disposed in apertures formed in the first guide bracket 34 and the second guide bracket 36 mounted to support arm 24.

Attached to and extending from below the fixture base 70 are a first leg 62 and a second leg 64. The first and second legs 62 and 64 can be spaced apart a distance that can be similar to the distance between a toddler's lower legs when standing. The first and second legs 62 and 64 can be substantially rigid in order to replicate the rigidity of the bone structure of a young child.

Disposed at the end of each of the legs 62 and 64 is a foot 66 and 68, respectively. The first foot 68 extends from the first leg 62, and the second foot 66 extends from the second leg 64. Each foot 66 and 68 can include a generally planar bottom surface disposed perpendicular to the axis of each leg 62 and 64. The generally planar bottom surface of each foot 66 and 68 can be used as the contact surface for contacting the surface of a mattress to be tested. The first and second feet 68 and 66 can be formed so as to replicate the general outline of a child's foot in some embodiments of the present disclosure. As shown in FIGS. 1 and 3, the first foot 68 is generally shaped like the outline of a child's left foot, and the second foot 66 is generally shaped like the outline of a child's right foot. The feet 66 and 68 are so disposed on the legs 64 and 62, respectively, such that the ends of each leg are aligned closer to the back of each foot. As shown in FIGS. 9-12, a flexible covering can be placed on each foot 66 and 68. In the embodiment shown in FIGS. 9-12, the flexible coverings are children's shoes 65 and 67; however, other flexible coverings can alternatively be used. The flexible coverings can be provided on the bottom surfaces of the feet 66 and 68 to replicate the soft pads of the lower surfaces of a child's feet. The length of the feet can range in size from approximately 7 cm to approximately 13 cm. Other lengths are contemplated and encompassed by the present disclosure.

As shown in FIGS. 9-12, the fixture base 70 can serve as a platform on which one or more detachable load member 41 can be disposed. The detachable load members can be of known masses so that the mass of the fixture can be adjusted to pre-determined amounts. When gravity is employed in the generation of force to be applied to the mattress sample, the load members can be used to produce a pre-determined force to be applied in each cycle. The mass of the fixture can range in size to mimic the mass of a toddler. For example, the mass range of the fixture can be from about 3 kg to about 8 kg. Alternatively, the mass range of the fixture can be from about 3.5 kg to about 7.5 kg. Furthermore, the mass range of the fixture can be from about 4 kg to about 6.5 kg.

The fixture 60 is supported on the apparatus 10 by a cable 30. As shown in FIGS. 2 and 3, the eyelet 33 is disposed in and extends from the fixture base 70. The cable 30 is fixed to the fixture 60 at the eyelet 33. The fixture 60 is suspended by the cable 30 and is movable relative to the rest of the apparatus 10.

Figure 10:
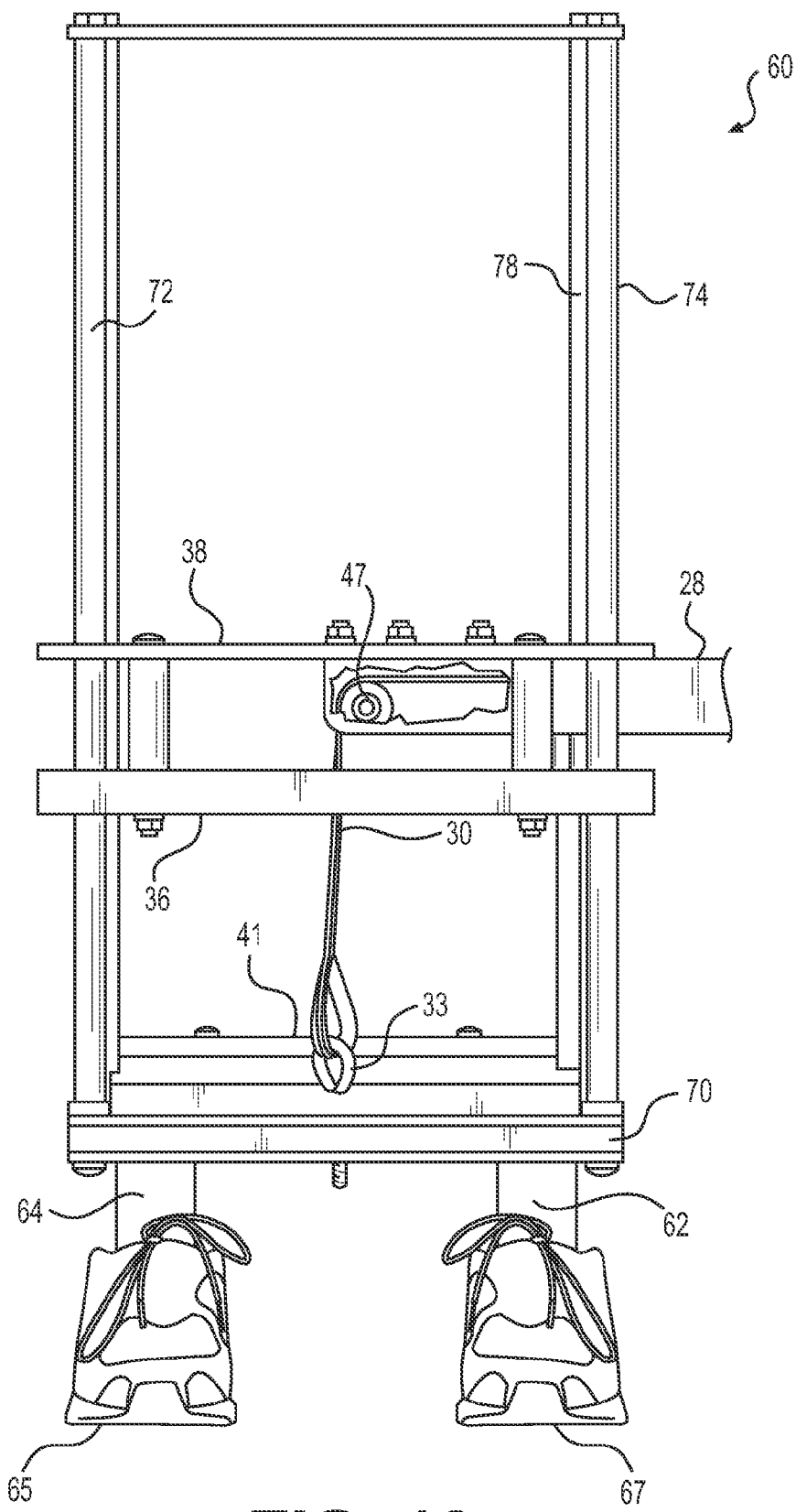
FIG. 10 is a side elevation view of a portion of the testing apparatus of FIG. 9.
Figure 11:
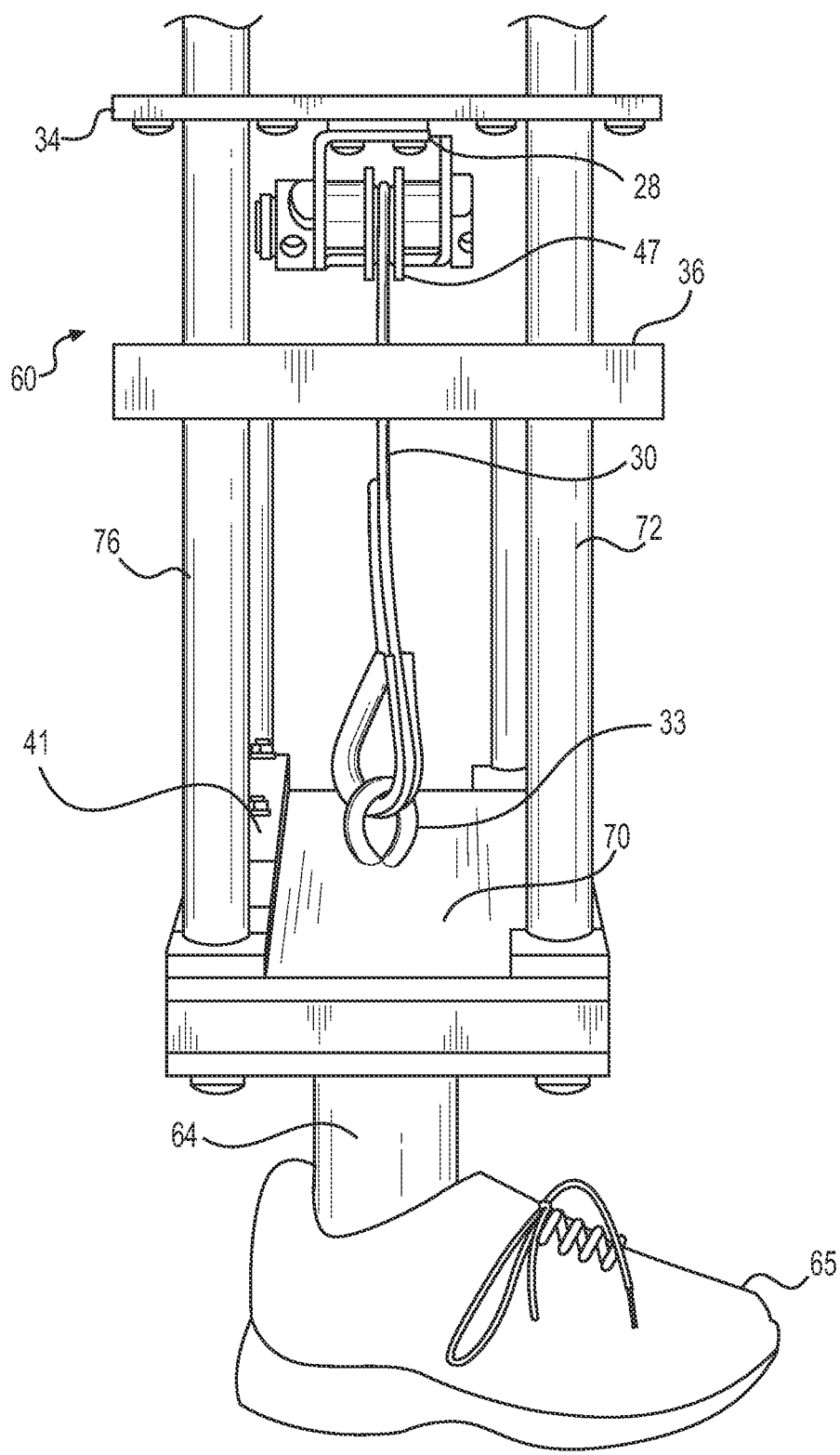
FIG. 11 is a side perspective view of a portion of the testing apparatus shown in FIG. 9.

The cable 30 is mounted on a series of pulleys as shown in FIGS. 10 and 11. A first pulley is disposed at the end of horizontal member 28 of the support arm 24. The cable 30 extends along the interior of the support arm 24. A second pulley is disposed at the juncture of the horizontal member 28 and the vertical member 26 of the support arm 24. The cable 30 extends down along a portion of the length of vertical member 26 to an opening formed therein. A third pulley 47 is disposed adjacent the opening in the vertical member 26. A portion of the cable 30 extends perpendicularly from the vertical member 24 to the cable assembly.

Figure 4:
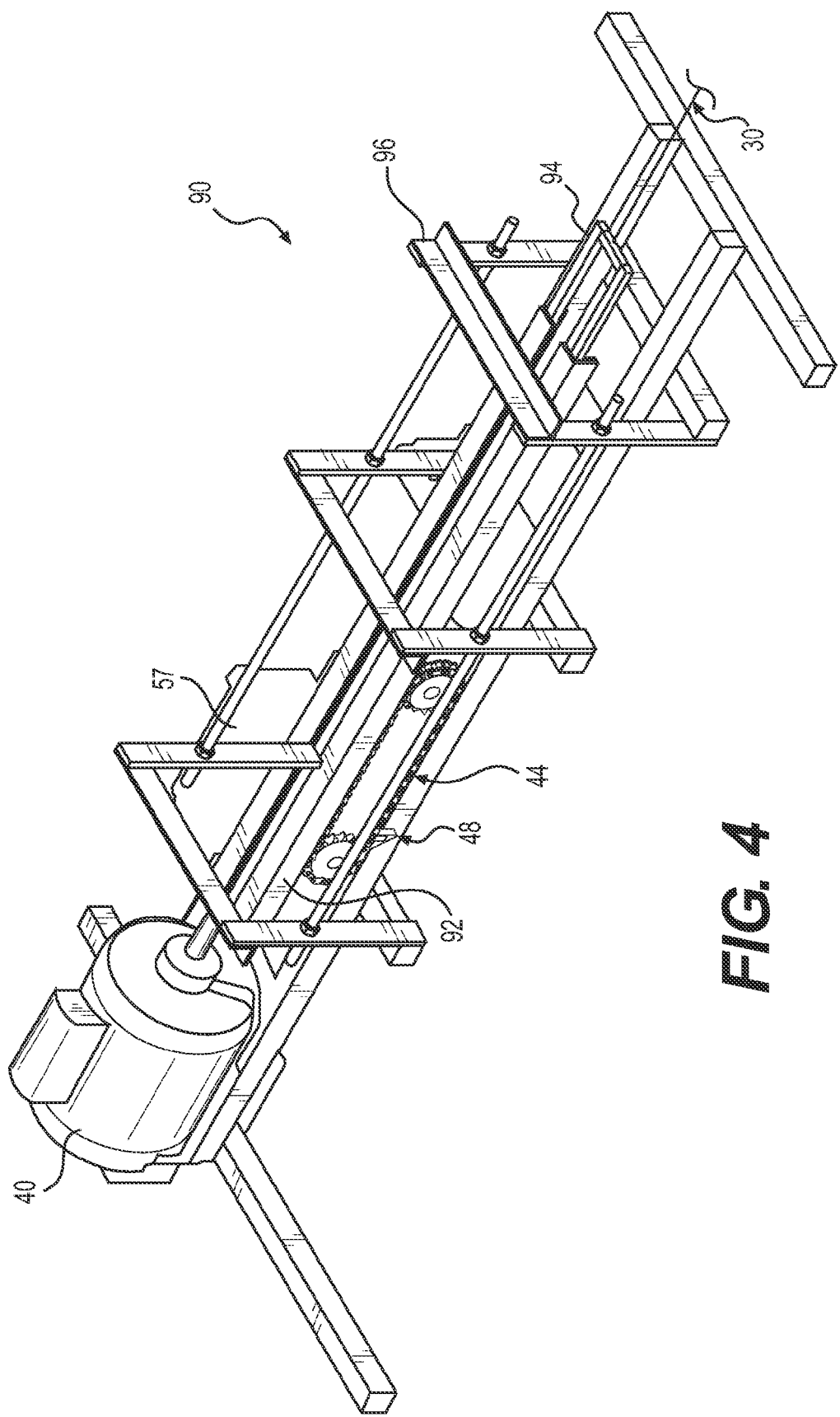
FIG. 4 is a perspective view of a motor, drive assembly, and cable assembly of a testing apparatus encompassing aspects of the present disclosure.
Figure 6:
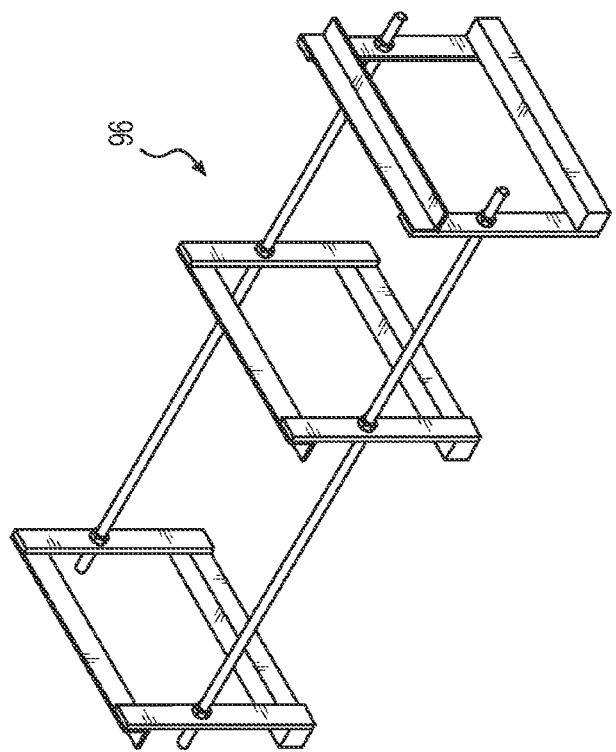
FIG. 6 is a perspective view of a raceway support portion of the cable assembly of the testing apparatus set forth in FIG. 1.
Figure 5:
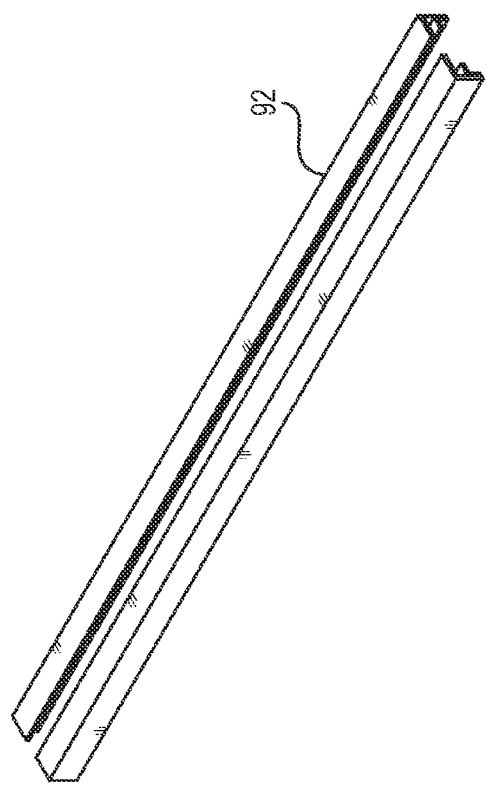
FIG. 5. is a perspective view of a raceway portion of the cable assembly of the testing apparatus set forth in FIG. 1.
Figure 8:
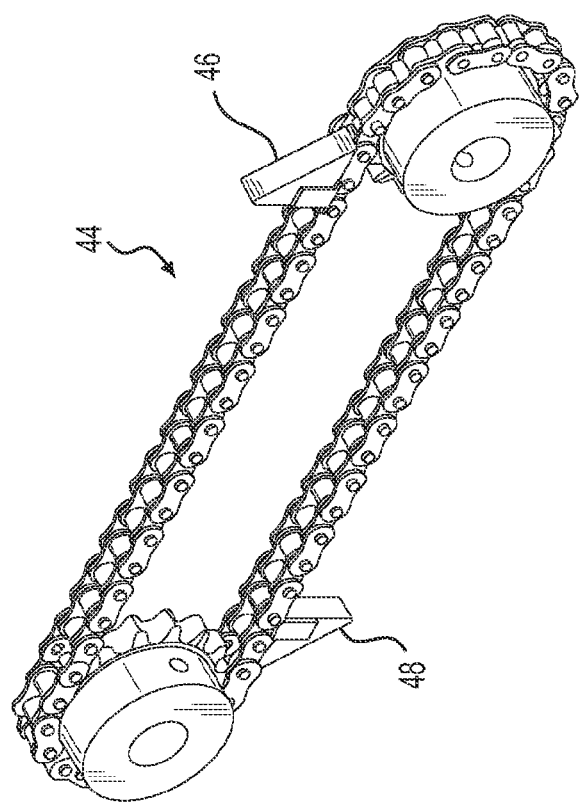
FIG. 8 is a drive assembly of the testing apparatus set forth in FIG. 1.
Figure 7:
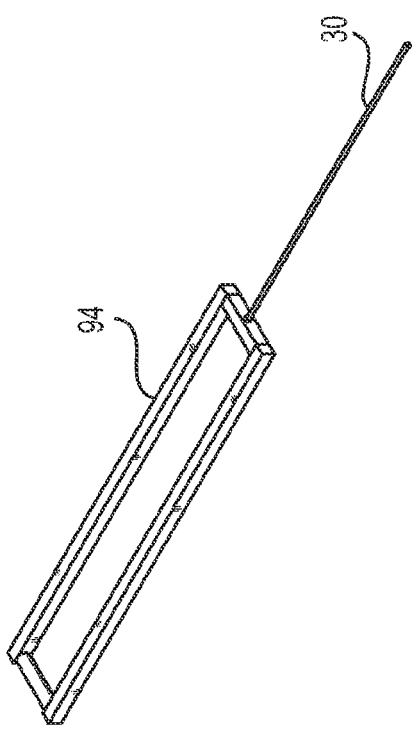
FIG. 7 is a shuttle portion of the cable assembly of the testing apparatus set forth in FIG. 1.
Figure 9:
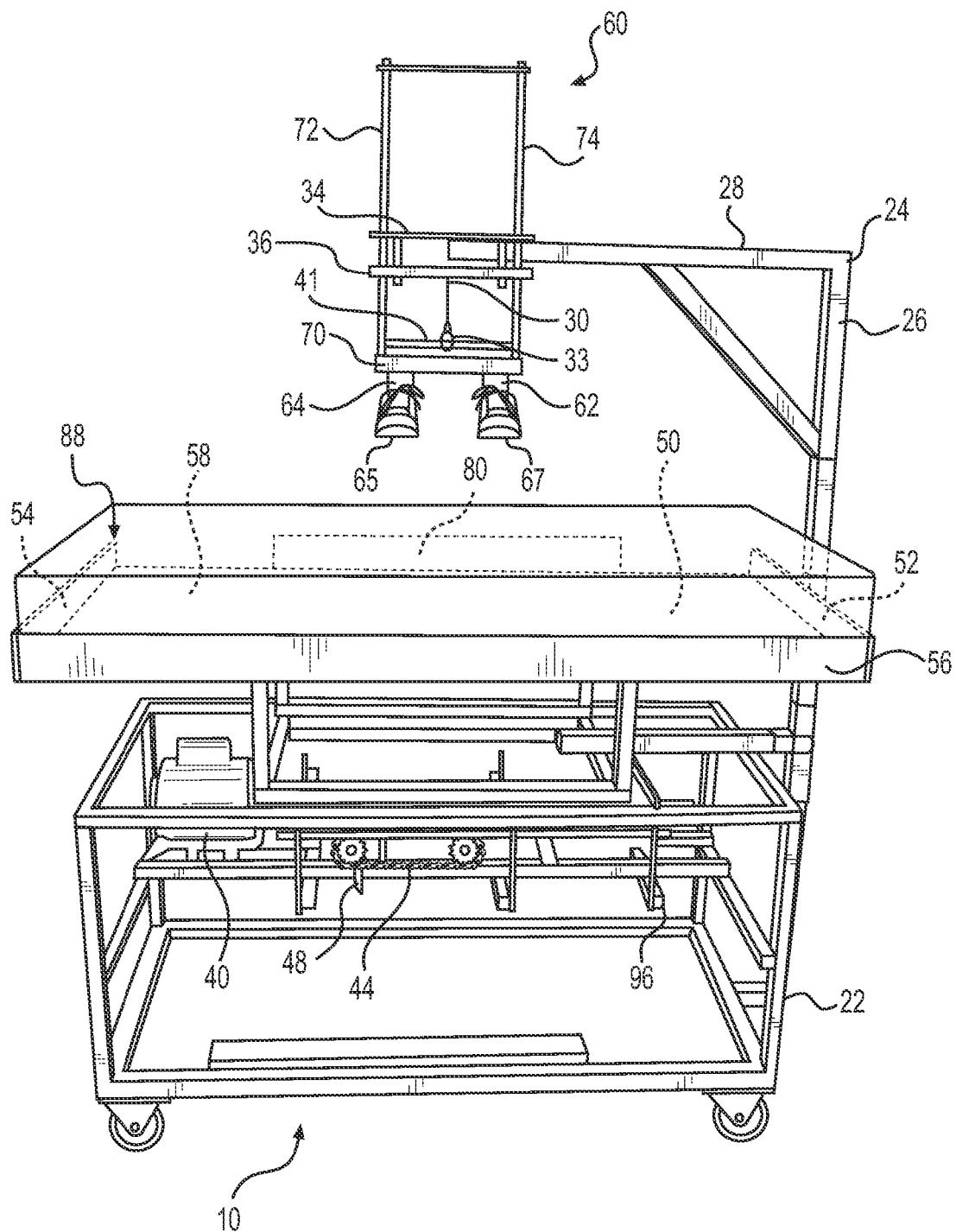
FIG. 9 is a perspective view of a testing apparatus encompassing aspects of the present disclosure.

The cable assembly includes a shuttle 94 to which the cable 30 is attached as shown in FIG. 7. The shuttle 94 is movably aligned within a raceway 92 as the one shown in FIG. 5. The raceway 92 is mounted on a raceway support 96 as shown in FIGS. 1, 2, and 4. The shuttle 94 and raceway 92 are so aligned as to allow for the engagement of one of two fingers or catches 46 and 48 spaced along the length of a continuous chain loop 44. The continuous or chain loop 44 is movably mounted on a pair of sprockets as shown in FIGS. 2 and 9. At least one of the sprockets is movably connected to a speed reducer 57 that is in turn movably connected to the motor 40. When the roller chain loop 44 cycles, one of the catches 46 and 48 engages the shuttle 94, thereby moving it and the end of the cable 30 in the direction of the motor 40. As the cable 30 moves, the fixture 60 is raised to a predetermined height. As the chain loop 44 turns, the catch then disengages the shuttle 94, thereby releasing the shuttle 94, which is pulled back to its original position by the weight of fixture 60 attached to cable 30. When the catch 46 releases the shuttle 94, the fixture 60 falls from a pre-determined height striking a sample of a mattress disposed on the sample support member 50. The feet 66 and 68 contact pre-selected portions of the sample and apply a predetermined force thereto. More specifically, the foot 66 contacts a first portion of the top surface of the mattress and the foot 68 contacts a second portion of the top surface of the mattress. The force applied is predetermined from a calculation of the mass and maximum height of the fixture 60. As the chain loop 44 spins through its cycle, the catch 48 then engages the shuttle 94 thereby moving it again toward the direction of the motor 40. This movement causes the fixture 60 to rise, since the cable 30 suspends it. The feet 66 and 68 then disengage the first and second portions of the top surface of the mattress sample to which force had been applied. The raising of the fixture 60 to the pre-determined height after the single application of a predetermined force constitutes a single cycle. Multiple cycles can thereby be executed. The cycles may be carried out for a pre-determined number of cycles or for a predetermined amount of time. The pre-determined height can, for example, be approximately 0.25 m. Other heights are contemplated by the present disclosure.

The motor 40 can be a low power motor sufficient to move the cable 30 and fixture 60. In one embodiment, the motor 40 is a 0.5-horse power, single phase, 115 V electric motor. The motor 40 can be coupled to a speed reducer 57. In one embodiment, the speed reducer 57 is a 30-to-1 speed reducer, although other configurations are contemplated by the present disclosure.

As shown in FIGS. 9 and 12, a sample mattress 88 can be placed on the mattress support member 50 in various positions. In FIG. 9, the sample mattress 88 is aligned with the sidewall 80 up in the vertical position, whereas in FIG. 12, the sample mattress is aligned with the sidewall 80 moved down into a horizontal position. In this manner, various parts of the sample mattress can be placed under the fixture 60 and tested.

Figure 13:
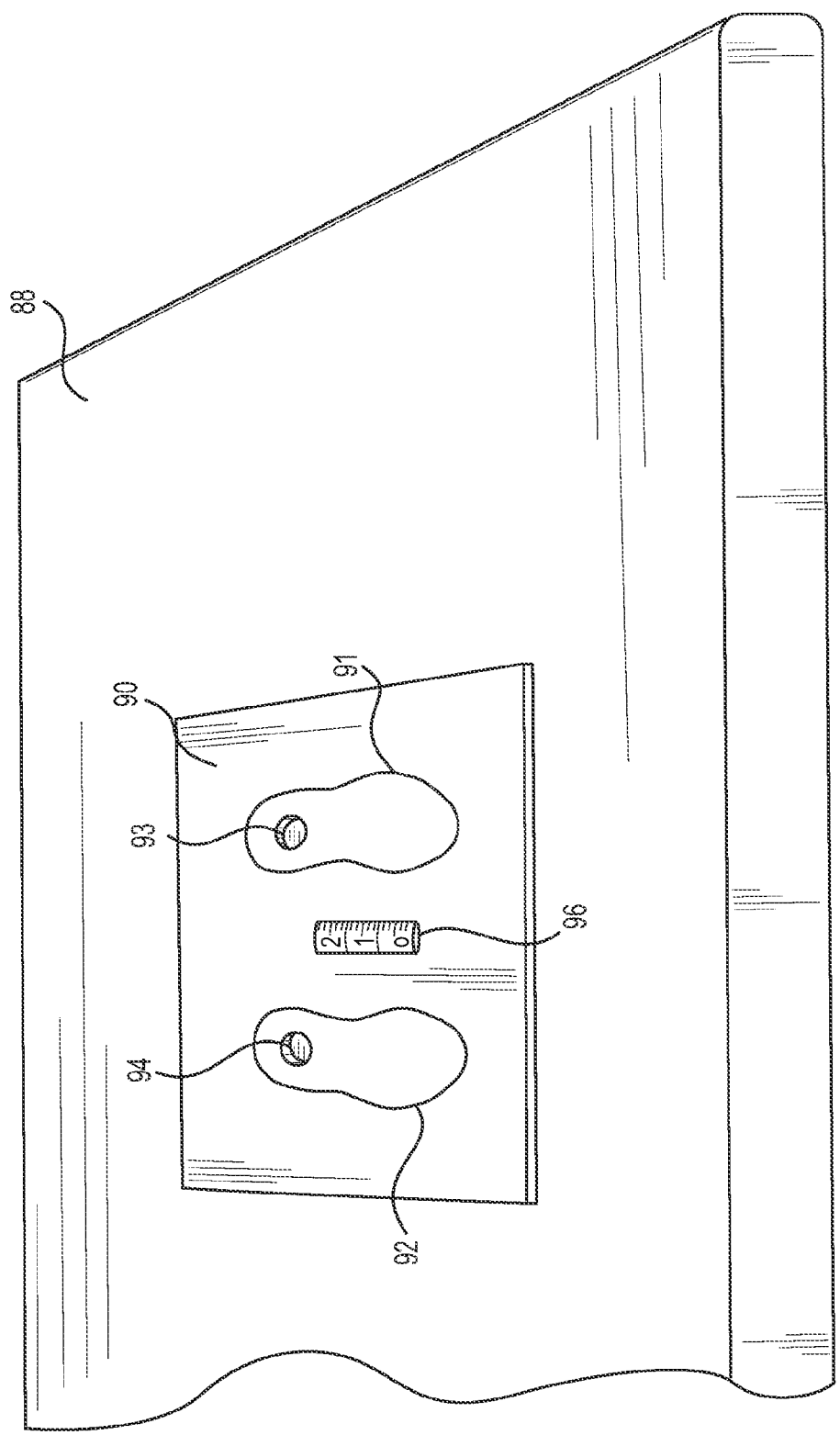
FIG. 13 is a perspective view of a platen and measurement form encompassing aspects of the present disclosure atop a mattress.

FIG. 13 shows a sample mattress 88 with two testing tools placed thereon. The first of the two testing tools is a platen 90 having a pair of foot or shoe prints 91 and 92 formed thereon. The first shoe print 91 is generally sized and shaped similar to a typical toddler's left shoe; and, likewise the second shoe print 92 is sized and shaped similarly to a typical toddler's right shoe. The platen 90 also comprises a pair of openings, a first opening 93 and a second opening 94 formed therein. Each of the first and the second openings 93 and 94 extends completely through the platen 90. The first opening 93 is disposed within the first shoe print 91 and the second opening 94 is disposed within the second shoe print 92. Each of the openings 93 and 94 are aligned generally in the heal area of their respective shoe prints 91 and 92. More particularly, each of the openings 93 and 94 can be aligned generally in the section of the shoe prints 91 and 92 that would correspond to where each leg of the testing apparatus attached to the respective foot of the fixture of the testing apparatus. For the forces imparted by the testing apparatus to a sample mattress could, in some instances, be greatest in the vicinity of the attachment point of each leg to the respective foot, and likewise the forces imparted to a mattress by a jumping toddler could, in some instances, be greatest where the heal sections of the toddler's feet strike the mattress.

The platen 90 is shown generally square; however, the present disclosure encompasses platens of various shapes. The measurement form 96 is marked with measurement indicia of sufficient gradations to allow for accurate measurement of mattress deformation. For example, the measurement form 96 can be marked with centimeter and millimeter markings or, alternatively, inch and fractions of an inch markings to allow for relevant measurement of mattress deformation. Alternatively, the measurement form can have no measurement marking formed thereon. The measurement form also can be of a pre-determined weight. As shown in FIG. 13, the measurement form 96 is a cylinder of a pre-determined mass; however, the present disclosure encompasses measurement forms of various, sizes, shapes, and masses.

Figure 14:
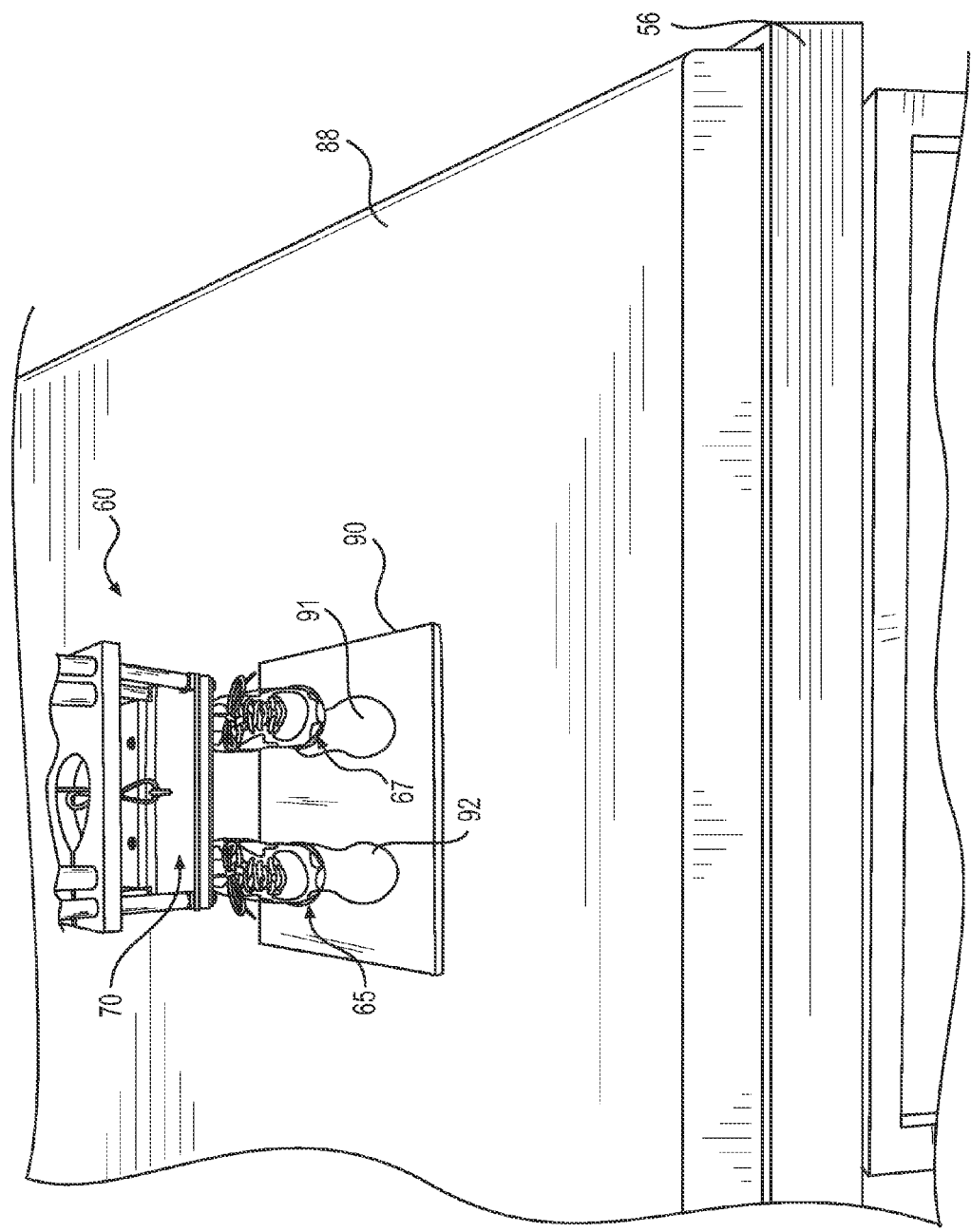
FIG. 14 is a perspective view of the platen and mattress shown in FIG. 13 disposed on a testing apparatus encompassing aspects of the present disclosure.
Figure 15:
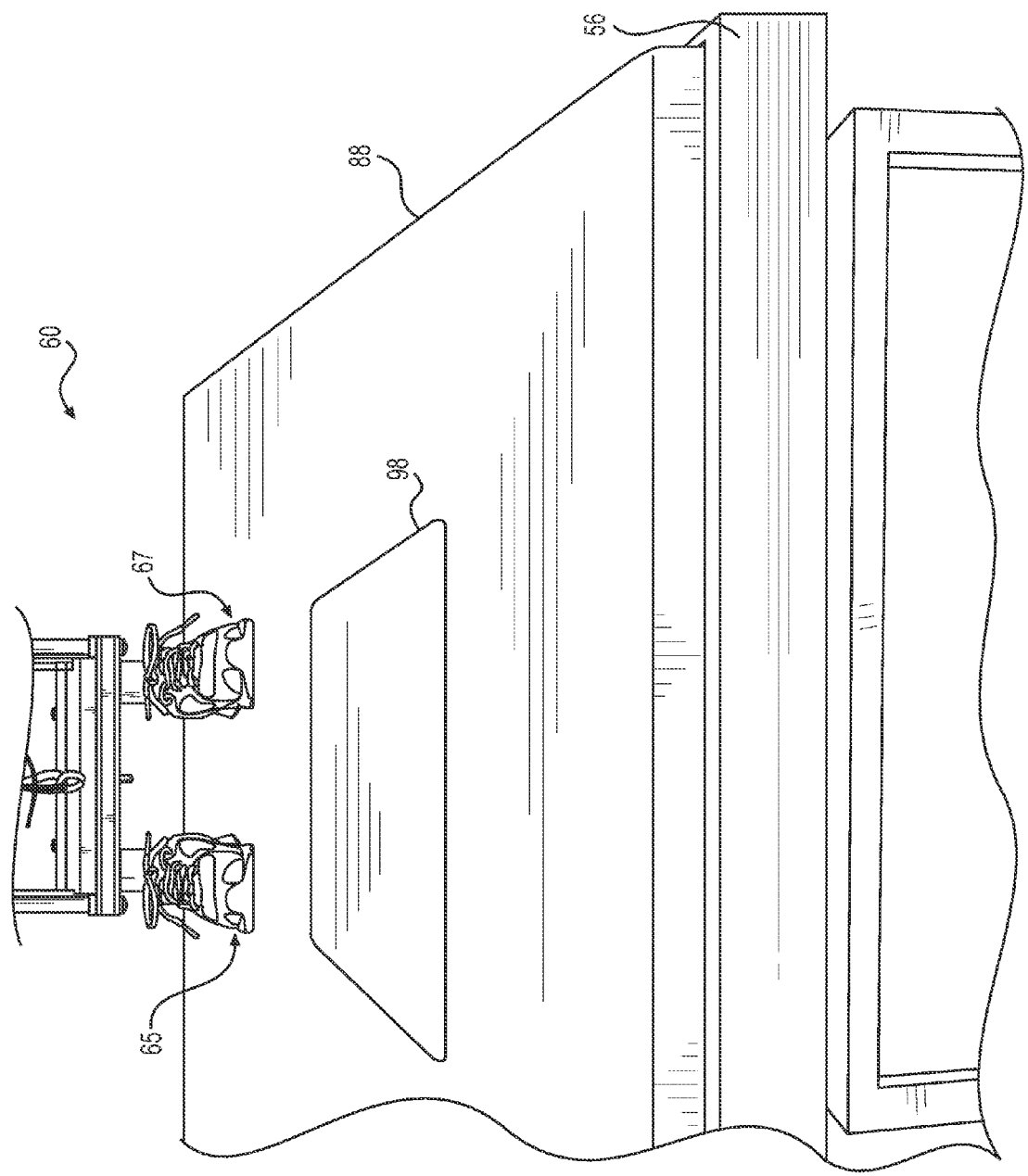
FIG. 15 is another perspective view of the mattress and testing apparatus shown in FIG. 14 with the platen removed therefrom.

FIG. 14 shows the mattress 88 disposed on a testing apparatus, a portion of which is visible, and a platen 90 disposed on the top surface of the mattress 88. The mattress 88 and platen 90 are arranged on the testing apparatus so that the platen 90 is disposed below the fixture 60. More particularly, the platen 90 is arranged on the top surface of the mattress 88 such that the first and second shoe prints 91 and 92 are aligned, respectively, with the shoes 65 and 67, each of which covers one of the two feet of the fixture 60. Once the mattress 88 and platen 90 are so arranged, the outline of the platen 90 can be marked directly on the top surface of the mattress 88. As shown in FIG. 15, the outline 98 of the platen is marked on the mattress 88 below the fixture 60. By marking the outline 98 of the platen directly on the mattress 88. Post testing measurement of the exact area where the fixture contacted the mattress surface can be achieved.

Prior to cycling of the fixture 60, the measurement form 96 is placed in each of the openings 93 and 94 formed in the platen 90. The bottom of the cylinder 96 is placed directly on the top surface of the mattress 90 and the depth of the cylinder within the opening is noted by determining the closest mark to the top surface of the platen.

Figure 16:
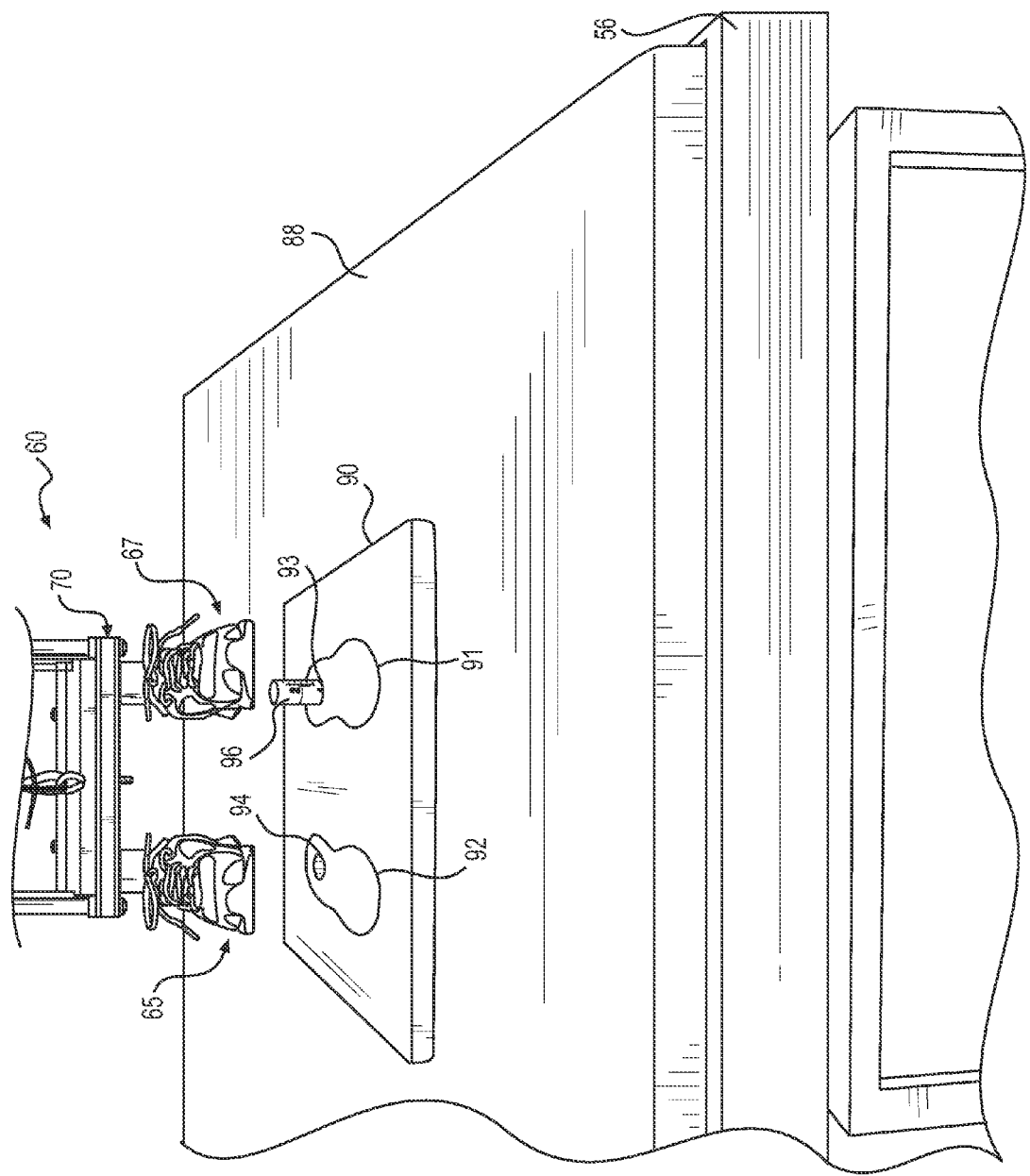
FIG. 16 is a perspective view of the mattress and testing apparatus shown in FIG. 14 with the platen and measurement form shown in FIG. 13 disposed thereon.

As shown in FIG. 16, after the testing apparatus has been cycled the appropriate number of cycles, the testing apparatus can be stopped and the platen 90 replaced on the top surface of the mattress 88. The platen 90 is placed exactly over the outline 98 that was previously marked. The measurement form 96 can then be placed again in each of the openings 93 and 94 so that the bottom surface of the cylinder rests on the top of the mattress 88 and the depth of the cylinder is measured at the top surface of the platen.

The methods of the present disclosure are directed in part to assessing the durability of a crib mattress or other child development support surface. The methods can assess various aspects of a crib mattress, including, but not limited to, the durability of a crib mattress ticking and/or filling. The durability of the crib mattress can be assessed over the expected life of the product using the methods contemplated by the present disclosure. Certain aspects of the safety of a crib mattress also can be assessed by certain embodiments of the methods contemplated by the present disclosure. For example, the possible risks associated with an expanding gap between a crib and a mattress resulting from changes in the mattress caused by extended use can be assessed. Also, risks associated with the formation of depressions resulting from extended use can be assessed.

In one embodiment, a method for testing a crib mattress, mattress material, or child development surface can include: selecting a sample of a crib mattress or filling material; aligning the sample in a test position relative to the testing apparatus; and, applying a pre-determined force to a portion of the sample; and removing the force from the portion of the sample. The method also can include applying a second pre-determined force to the portion of the sample and removing the second pre-determined force from the portion of the sample. The method also may include applying and removing a force to the portion of the sample, wherein the applying and removing of the force constitutes one cycle. Further, the method can include executing a pre-determined number of cycles. Alternatively, the method can include executing cycles for a predetermined amount of time.

The present disclosure encompasses a method for testing a crib mattress that can comprise the steps of selecting a sample of a crib mattress or filling material, placing the sample directly on the mattress support member of a testing apparatus, provided that the sample is at least about 15 cm or greater. For a sample with a thickness other than approximately 15 cm., the sample can either be placed on a flat rigid board of appropriate thickness that is then placed on the mattress support member, the mattress support member itself can be adjusted, or the fixture of the apparatus can be adjusted to a pre-determined height above the surface of the sample. The method also can include adjusting the distance of the fixture to a predetermined distance from the surface of the sample (in one example, the distance can be approximately 20 cm.), cycling the apparatus for a predetermined time period, wherein force is applied and removed multiple times to a portion of the sample surface, measuring the depth of the depression formed in the portion of the sample surface to which force was applied. In one example, the measuring step can include placing a straight edge that is at least 1.2 m in length and 5 cm in width on the surface of the test sample, and then measuring the distance between the straight edges' lower surface and the test sample's surface within the depressions that have formed due to the pounding of the feet of the fixture. In this case, the maximum depressions depth is measured.

Alternatively, the method also can include the steps of repeating the cycling and measuring steps of the testing procedure for multiple time periods. In one example, five time periods are assessed, including at the beginning, after one hour of cycle time, after four hours of cycle time, after eight hours of cycle time, and after twenty-four hours of cycle time. These time periods correspond to approximately 3120, 12480, 24960, and 74880 simulated jumps respectively.

The method also can include the step of aligning the sample to a second predetermined test position. This realignment can be accomplished in one example by adjusting the movable arms operably connected to the sample support and realigning the sample thereon. In one particular embodiment, the sample is realigned so as to allow for the testing of a portion of the sample surface adjacent the edge of the sample.

The steps of cycling the raising and dropping of the fixture and subsequent measurement for multiple time periods. In one example, the time periods can include at zero hours, one hour, four hours, eight hours, and twenty-four hours. When testing a portion of the surface of the sample mattress adjacent the edge of the sample, a second measurement can be performed after each time period. The second measurement generally can include measuring the depth of a depression formed in the sidewall of the sample. In one embodiment, the measurement can include placing the straight edge along the border of the sample at the samples' upper edge. The distance from the edge of the straight edge to the edge of the test surface is measured. The total gap distance can be determined by adding the original distance between the crib wall and the mattress sidewall.

The method can include the step of re-measuring all test depressions after approximately twenty-four hours after the final force cycle. This step can be used to assess the recovery of the sample material.

In an alternative test procedure, a mattress 88 to be tested is placed on the mattress support member 50 of the test apparatus 10 aligning the portion of the mattress 88 to be tested under the fixture 60 of the test apparatus 10. A platen is placed flat on the top surface of the mattress directly under the fixture 60, and its position on the mattress is marked for later reference. The platen has two openings formed therein that correspond to the point of most extensive contact of each foot of the fixture with the mattress when the fixture is dropped on the mattress. A cylindrical weight with a calibrated height is inserted into each of the two openings. The depth of the weight, measured from the top surface of the platen to the top surface of the sample mattress 88, is recorded in each opening prior to the beginning of the test cycle. This measurement can be taken by marking the point along the length of the cylindrical weight where the top edge of the platen meets the sidewall of the weight, and then measuring the distance from this point to the bottom edge of the weight. The platen is then removed from the top surface of the mattress 88 to be tested.

The test cycle begins by activating the motor 40 of the apparatus 10. The motor 40 turns a gear that drives the chain loop 44 on which is formed at least one catch 46 and 48. The first catch 46 engages a shuttle 94 that moves along the raceway 92 and is attached to the cable 30. The cable 30, in turn, attached to the fixture 60, raises the fixture 60 from a first position proximal to the mattress support member 50 to a second position distal the mattress support member 50 an and of a predetermined height. Once the catch 46 disengages the shuttle 94, the fixture 60 falls by gravity. The contact forms, in this case two feet 66 and 68 aligned parallel and extending from the bottom of the fixture 60, strike the sample mattress at the predetermined first position that was previously measured using the weight and the openings in the platen. As the motor drives the chain loop 44, the second catch 48 engages the shuttle 94, thereby again raising the fixture 60 from the first position vertically to the second position, thereby beginning another cycle. This cyclical process can be repeated for a predetermined period of time.

Once the predetermined cycle time is completed, the platen is repositioned in its original marked position on the sample mattress, the calibrated weight is reinserted into the holes in the platen, and the depth of the weight in the hole is re-measured. Both the initial measurement and the subsequent measurement are noted and the differential determined. The differential represents the deformation that a mattress could experience during normal use by a toddler. The cyclical period of repeated fixture drops can be continued after the second measurement with one or more re-measurements being conducted after predetermined periods of time. Alternatively, after a pre-determined period of time after the second measurement during which the mattress is not subjected to the operation of the apparatus, a third measurement can be conducted to determine the recovery of the mattress from the deflection noted in the second measurement.

For example, a second measurement can be conducted after approximately four hours after the initial measurement and during which time the mattress is subjected to the forces applied by the apparatus during its cycling phases. A third measurement can be carried out fifteen minutes after the second measurement. During this fifteen-minute interim period, the apparatus is not operated and the mattress is allowed to recover. It has been determined that cycling the apparatus during a four-hour time period provides wear similar to that a mattress experiences during approximately three years of use, wherein a three-year use period is typical of the time in which a child will use a crib mattress.

Alternatively, the third measurement can be taken approximately twenty-four hours from the initial measurement, and during which time the mattress is subjected to the forces applied during the cycling of the apparatus. Other time periods and numbers of re-measurements are contemplated and encompassed by the present disclosure. The test results, including the differentials representing possibly permanent deflections in the mattress, can be compared to other samples of the same model mattress, as well as other types of mattresses to determine the expected durability and resilience of a model or a sample.

EXAMPLES

Sample mattresses were tested according to the test procedure set forth above. The results of the test examples are set forth below with measurements being approximate due to the conversion to SI units and rounding of the results.

Example 1

Sample: Polyurethane Foam Crib Mattress

|  | START | AFTER 4 HOURS | 4 HOUR DIFFERENTIAL | AFTER 4.25 HRS. | 4.25 HOUR DIFFERENTIAL |
| --- | --- | --- | --- | --- | --- |
| Left Contact (m) | 0.0222 | 0.0238 | 0.0016 | 0.0238 | 0.0016 |
| Right Contact (m) | 0.0222 | 0.0238 | 0.0016 | 0.0238 | 0.0016 |

Example 2

Sample Innerspring Crib Mattress

|  | START | AFTER 4 HOURS | 4 HOUR DIFFERENTIAL | AFTER 4.25 HRS | 4.25 HOUR DIFFERENTIAL |
| --- | --- | --- | --- | --- | --- |
| Left Contact (m) | 0.0222 | 0.0238 | 0.0016 | 0.0238 | 0.0016 |
| Right Contact (m) | 0.0238 | 0.0267 | 0.0032 | 0.027 | 0.0254 |

Example 3

Sample: Polyester Foam Block

|  | START | AFTER 4 HOURS | 4 HOUR DIFFERENTIAL | AFTER 4.25 HRS | 4.25 HOUR DIFFERENTIAL |
| --- | --- | --- | --- | --- | --- |
| Left Contact (m) | 0.0222 | 0.0318 | 0.0094 | 0.0302 | 0.0079 |
| Right Contact (m) | 0.0222 | 0.0318 | 0.0094 | 0.0302 | 0.0079 |

While the deflections evidenced in the differentials determined after fifteen minutes and four hours could be considered acceptable in the case of the polyurethane foam crib mattress and the innerspring crib mattress, the deflections evidenced by the polyester foam block could be considered unacceptable for some uses, such as a crib mattress. As shown by these examples, the apparatus and methods of the present disclosure can be used to determine the durability and resilience of a crib mattress or other child development surface, as well as determine the suitability of some articles for such uses.

While the present disclosure includes embodiments directed to crib mattresses and other flexible child development platforms and surfaces, it is contemplated that the disclosed apparatus and methods can be applied to the evaluation of different types of furniture and components thereof, including, but not limited to, adult sized mattresses, sofas, chairs, and other furniture having flexible surfaces. The present disclosure contemplates and encompasses modifications and variations to the apparatus and methods disclosed herein.

What is claimed is:

1. A method of testing a crib mattress comprising the steps of:
   aligning a mattress under a fixture of a test apparatus;
   placing a platen on a top surface of the mattress, wherein the platen comprises a first opening and a second opening formed therein, and wherein each of the first and the second openings are aligned over one of a first position and a second position on the top surface of the mattress;
   placing a measurement form in the first opening, wherein the measurement form contacts the top surface of the mattress;
   measuring a first distance from the top surface of the mattress to a first pre-determined point on the platen;
   placing the measurement form in the second opening, wherein the measurement form contacts the top surface of the mattress;
   measuring a first distance from the top surface of the mattress to a second pre-determined point on the platen;
   contacting the first and the second positions on the top surface of the mattress with a fixture having a pair of feet formed thereon;
   removing the fixture from the top surface of the mattress;
   placing the platen on the top surface of the mattress, and wherein each of the first and the second openings are aligned over one of the first position and the second position on the top surface of the mattress;
   placing the measurement form in the first opening, wherein the measurement form contacts the top surface of the mattress;
   measuring a second distance from the top surface of the mattress to the first pre-determined point on the platen;

placing the measurement form in the second opening, wherein the measurement form contacts the top surface of the mattress;

measuring a second distance from the top surface of the mattress to the second pre-determined point on the platen;

determining a differential between the first distance and the second distance from the top surface of the mattress to the first pre-determined point on the platen; and, determining a differential between the first distance and the second distance from the top surface of the mattress to the second pre-determined point on the platen.

2. The method of claim 1, wherein the step of contacting the first and the second positions on the top surface of the mattress with a fixture having a pair of feet formed thereon further comprises dropping the fixture onto the top surface of the mattress from a predetermined height.

3. The method of claim 1, further comprising the step of marking a position of the platen on the top surface of the mattress.

4. The method of claim 1, wherein the first pre-determined point on the platen is a top edge of the first opening.

5. The method of claim 1, wherein the second pre-determined point on the platen is a top edge of the second opening.

6. The method of claim 1, wherein each of the first and the second openings are disposed within one of a first and a second shoe print formed on the platen.

7. The method of claim 1, wherein the first position and the second position are aligned below one of a first foot and a second foot of the pair of feet of the fixture.

8. The method of claim 1, wherein the step of measuring a first distance from the top surface of the mattress to a first pre-determined point on the platen further comprises reading the first distance from measurement indicia formed on the measurement form.

9. A method of testing a crib mattress comprising the steps of:

aligning a mattress under a fixture of a test apparatus;

placing a platen on a top surface of the mattress, wherein the platen comprises an opening formed therein, and the opening is aligned over a position on the top surface of the mattress;

placing a measurement form in the opening, wherein the measurement form contacts the top surface of the mattress;

measuring a first distance from the top surface of the mattress to a pre-determined point on the platen;

contacting the position on the top surface of the mattress with a fixture;

removing the fixture from the top surface of the mattress;

placing the platen on the top surface of the mattress, and wherein the opening is aligned over the position on the top surface of the mattress;

placing the measurement form in the opening, wherein the measurement form contacts the top surface of the mattress;

measuring a second distance from the top surface of the mattress to the pre-determined point on the platen; and, determining a differential between the first distance and the second distance from the top surface of the mattress to the pre-determined point on the platen.

10. The method of claim 9, further comprising the step of marking a position of the platen on the top surface of the mattress.

11. The method of claim 9, wherein the pre-determined point on the platen is a top edge of the opening.

12. The method of claim 9, wherein the step of measuring a first distance from the top surface of the mattress to a pre-determined point on the platen further comprises reading the first distance from measurement indicia formed on the measurement form.

13. The method of claim 9, wherein the step of contacting the position on the top surface of the mattress with a fixture further comprises dropping the fixture onto the top surface of the mattress from a predetermined height.

\* \* \* \* \*